United States Patent
Chao

(10) Patent No.: US 7,832,866 B2
(45) Date of Patent: Nov. 16, 2010

(54) EYE-TRACKING METHOD AND SYSTEM FOR IMPLEMENTING THE SAME

(75) Inventor: Shin-Min Chao, Jhonghe (TW)

(73) Assignee: Utechzone Co., Ltd., Jhonghe, Taipei County (TW)

( * ) Notice: Subject to any disclaimer, the term of this patent is extended or adjusted under 35 U.S.C. 154(b) by 0 days.

(21) Appl. No.: 12/506,100

(22) Filed: Jul. 20, 2009

(65) Prior Publication Data

US 2010/0103375 A1    Apr. 29, 2010

(30) Foreign Application Priority Data

Oct. 27, 2008  (TW) .............................. 97141172 A

(51) Int. Cl.
*A61B 3/14*    (2006.01)
(52) U.S. Cl. ....................................... 351/209; 351/246
(58) Field of Classification Search ................ 351/205, 351/206, 209, 210, 246
See application file for complete search history.

(56) References Cited

U.S. PATENT DOCUMENTS 4,836,670 A * 6/1989 Hutchinson ................. 351/210
5,708,862 A * 1/1998 Tsunekawa et al. .......... 396/51

* cited by examiner

*Primary Examiner*—Huy K Mai
(74) *Attorney, Agent, or Firm*—Ladas & Parry, LLP

(57) ABSTRACT

An eye-tracking method includes acquiring an image of an eye of a user, identifying a pupil of and a reflected light spot on the eye from the acquired image, determining a distance of the reflected light spot from a reference point on the pupil and an angle of the reflected light spot from an axis passing through the reference point on the pupil, determining a gazing point based on the distance and the angle and a pre-established set of data, and performing an operation associated with the gazing point. A system for implementing the eye-tracking method is also disclosed.

23 Claims, 5 Drawing Sheets

| r1 | r2 | r3 | r4 |
|----|----|----|----|
| r5 | r6 | r7 | r8 |
| r9 | r10 | r11 | r12 |
| r13 | r14 | r15 | r16 |

| r1 | r2 | r3 | r4 |
|----|----|----|----|
| r5 | r6 | r7 | r8 |
| r9 | r10 | r11 | r12 |
| r13 | r14 | r15 | r16 |

| r1 | r2 | r3 | r4 |
|----|----|----|----|
| r5 | r6 | r7 | r8 |
| r9 | r10 | r11 | r12 |
| r13 | r14 | r15 | r16 |

| r1 | r2 | r3 | r4 |
|----|----|----|----|
| r5 | r6 | r7 | r8 |
| r9 | r10 | r11 | r12 |
| r13 | r14 | r15 | r16 |

| r1 | r2 | r3 | r4 |
|----|----|----|----|
| r5 | r6 | r7 | r8 |
| r9 | r10 | r11 | r12 |
| r13 | r14 | r15 | r16 |

| r1 | r2 | r3 |
|----|----|----|
| r4 | r5 | r6 |

EYE-TRACKING METHOD AND SYSTEM FOR IMPLEMENTING THE SAME

CROSS-REFERENCE TO RELATED APPLICATION

This application claims priority of Taiwanese Application No. 097141172, filed on Oct. 27, 2008.

BACKGROUND OF THE INVENTION

1. Field of the Invention

This invention relates to an eye-tracking method, more particularly to an eye-tracking method that is non-invasive.

2. Description of the Related Art

In a conventional eye tracking technology, a contact lens mounted thereon with an inductance coil is worn by a user. When the user moves his/her eye, which in turn moves the inductance coil, a change in a magnetic flux occurs, whereby an electromotive force is generated from which an orientation of the eye of the user is determined. The contact lens, however, when worn by the user, irritates the eye of the user. Furthermore, since the contact lens has two layers, the contact lens, when worn by the user, impairs the vision of the user.

In another conventional eye tracking technology, electrodes are attached to a periphery of the eye of the user through which a voltage may be detected. When the user moves his/her eye, a change in the detected voltage occurs, whereby an orientation of the eye of the user is determined. The electrodes, however, when attached to the periphery of the eye of the user, causes discomfort to the user. Moreover, since secretions from the skin of the user have an affect upon the detected voltage, the orientation of the eye determined in this conventional technology is therefore inaccurate. Further, a relatively small voltage change is not detectable by this conventional technology.

In order to solve the above-mentioned problems, non-invasive eye-tracking technologies have been proposed. In one of the non-invasive eye-tracking technologies, the user wears a pair of eyeglasses, or a helmet, mounted thereon with a camera. The user, however, is required to maintain the position of the camera relative to the eye while using this conventional technology. This causes inconvenience on the part of the user. In another non-invasive eye-tracking technology, in which two charged-coupled device (CCD) cameras are used and complicated calculations are involved, high software and hardware implementation costs are incurred.

SUMMARY OF THE INVENTION

Therefore, an object of the present invention is to provide an eye-tracking method that can overcome the aforesaid drawbacks of the prior art.

Another object of the present invention is to provide a system for implementing the eye-tracking method.

According to an aspect of the present invention, an eye-tracking method, which is adapted to be implemented by a system, comprises:

A) while a user is gazing at a screen module and a light source emits light toward an eye of the user, configuring the system to acquire an image of the eye of the user captured by an image-capturing module;

B) configuring the system to identify a pupil of and a reflected light spot on the eye from the image acquired in step A);

C) configuring the system to determine a distance of the reflected light spot from a reference point on the pupil and an angle of the reflected light spot from an axis passing through the reference point on the pupil;

D) configuring the system to determine a gazing point based on the distance and the angle determined in step C) and a pre-established set of data obtained based on predefined regions on the screen module; and E) configuring the system to perform an operation associated with the gazing point.

According to another aspect of the present invention, a system, which is adapted to be coupled to an image-capturing module and a screen module, comprises a computing module and a processing module. The computing module is operable to acquire an image of the eye of the user captured by the image-capturing module while a user is gazing at the screen module and a light source emits light toward an eye of the user, to identify a pupil of and a reflected light spot on the eye from the image acquired from the image-capturing module, to determine a distance of the reflected light spot from a reference point on the pupil and an angle of the reflected light spot from an axis passing through the reference point on the pupil, and to determine a gazing point based on the distance and the angle determined thereby and a pre-established set of data obtained based on predefined regions on the screen module. The processing module is coupled to the computing module and is operable to perform an operation associated with the gazing point.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
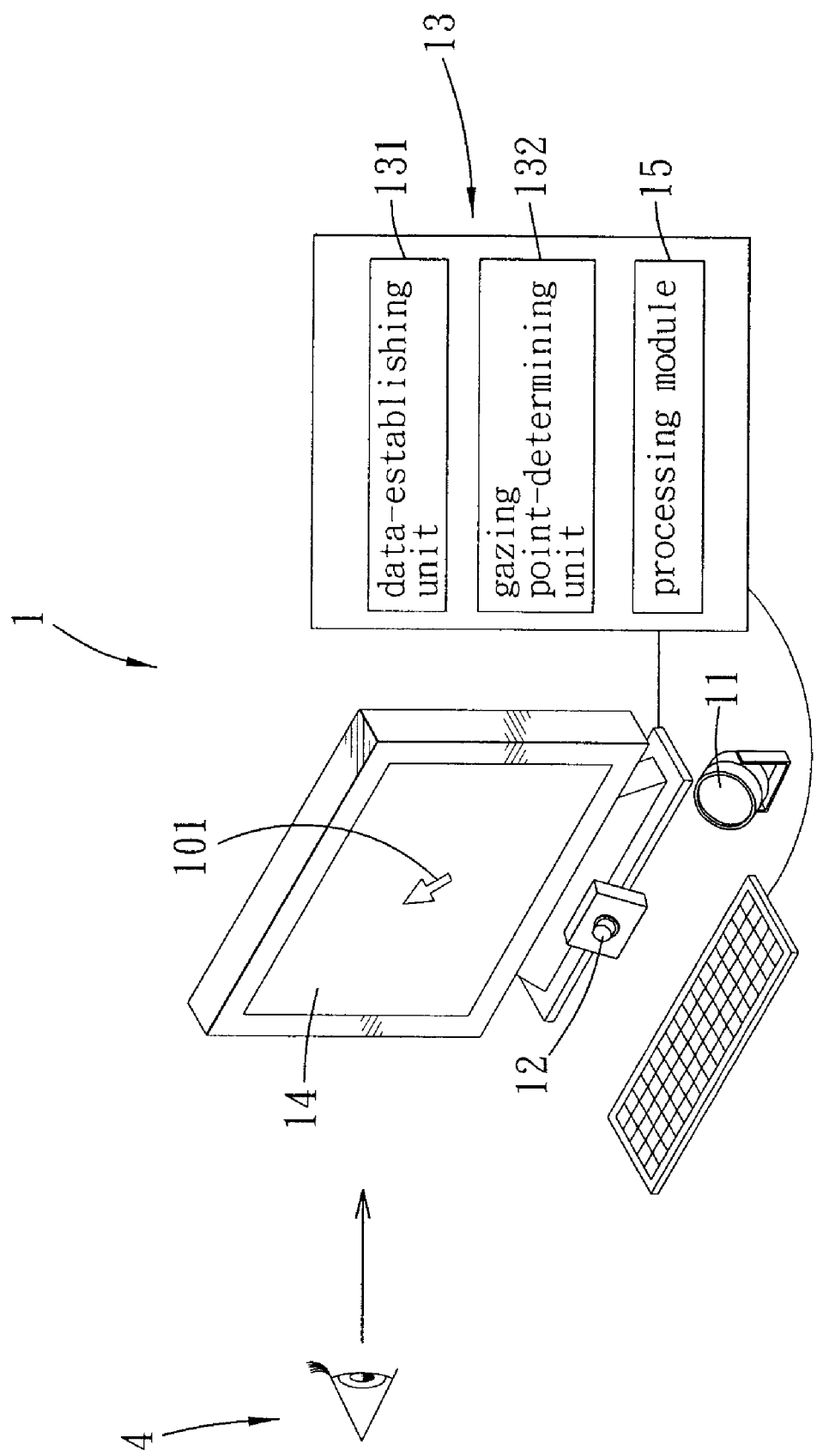
FIG. 1 is a schematic block diagram of the preferred embodiment of a system coupled to an image-capturing module and a screen module according to this invention.

Referring to FIG. 1, the preferred embodiment of a system 1 according to this invention is shown to include a computing module 13 and a processing module 15.

The system 1 is connected to an image-capturing module 12 and a screen module 14.

The computing module 13 includes a data-establishing unit 131 used for training the system 1 and a gazing point-determining unit 132 used during actual application of the system 1.

Figure 2:
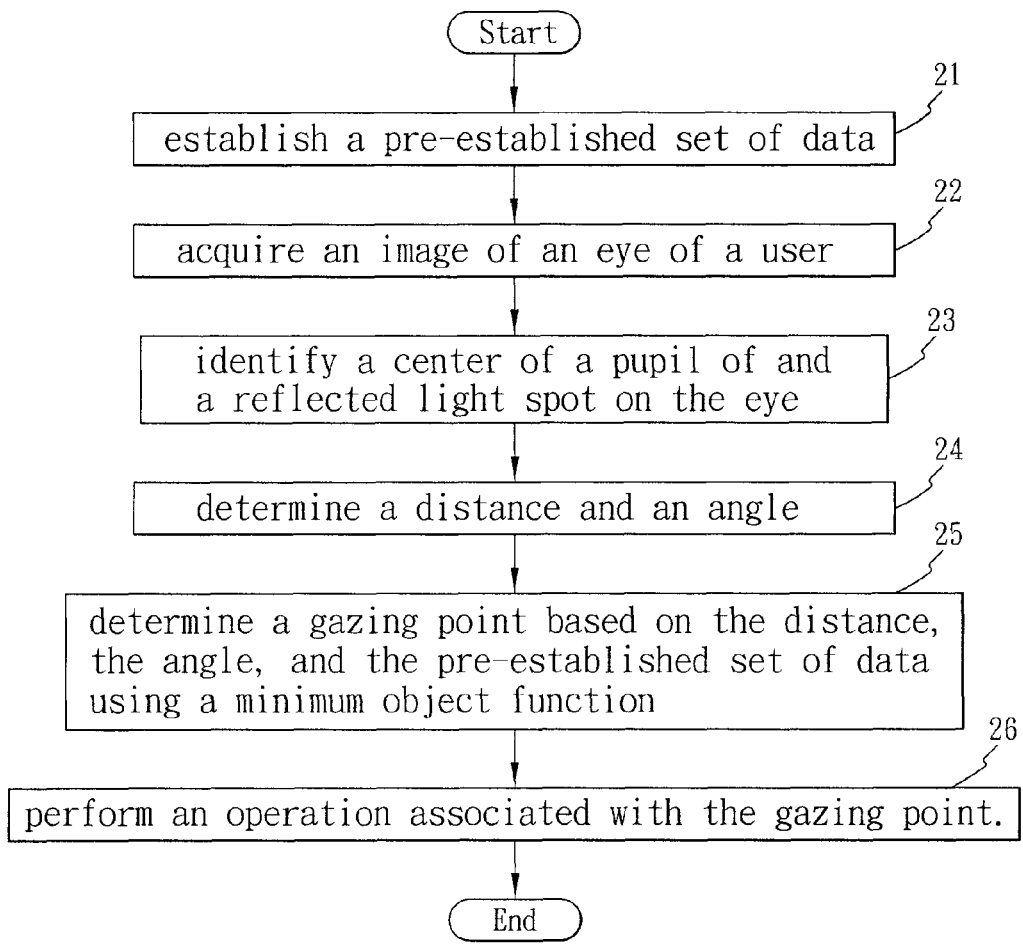
FIG. 2 is a flow chart of the first preferred embodiment of an eye-tracking method to be implemented by the system shown in FIG. 1 according to this invention.
Figure 3:
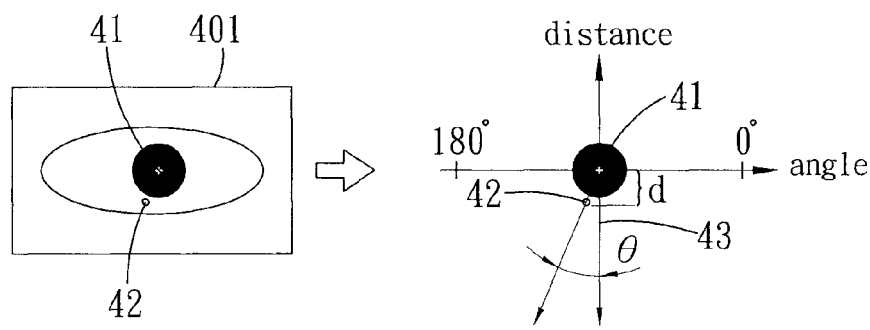
FIG. 3 is a schematic diagram illustrating a distance of a reflected light spot from a center of a pupil and an angle of the reflected light spot from a vertical axis passing through the center of the pupil.

The first preferred embodiment of an eye-tracking method to be implemented by the aforementioned system 1 according to this invention will now be described with further reference to FIGS. 2 to 4.

Figures 4, 5:
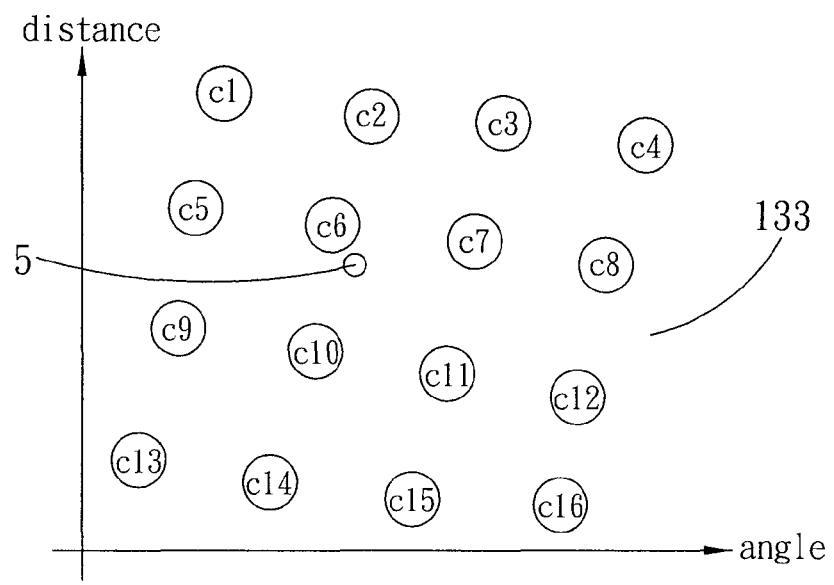
FIG. 4 is a graph representing candidate points in a pre-established set of data.
FIG. 5 is a schematic diagram illustrating the screen module when partitioned by the system into sixteen predefined regions.
Figure 6A:
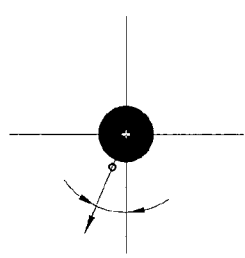
FIGS. 6a to 6d are schematic diagrams illustrating the screen module indicating the predefined regions in a sequential manner.
Figure 6B:
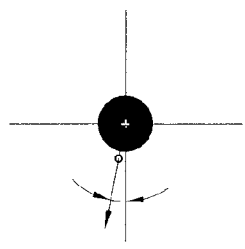
Figure 6C:
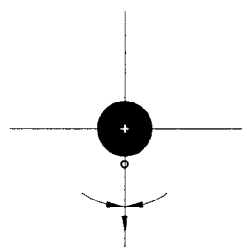
Figure 6D:
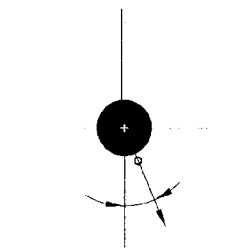

In step 21, the data-establishing unit 131 of the computing module 13 obtains a pre-established set of data 133;

In this embodiment, step 21 includes the following sub-steps:

a) partitioning the screen module 14 into predefined regions;

In this sub-step, as illustrated in FIG. 5, the screen module 14 is partitioned into sixteen predefined regions (r1 to r16) arranged in a four by four array.

b) controlling the screen module 14 to indicate, i.e., to show, one of the predefined regions (r1 to r16), e.g. the predefined region (r1);

c) while a user is gazing at the predefined region (r1) indicated in sub-step b) and a light source 11 emits light toward an eye 4 of the user, acquiring an image 401 of the eye 4 of the user captured by the image-capturing module 12;

d) identifying a center 41 of a pupil of and a reflected light spot 42 on the eye 4 from the image 401 acquired in sub-step c);

In this sub-step, the coordinates of the center 41 of the pupil and the coordinates of the reflected light spot 42 are identified. Moreover, in this sub-step, the center 41 of the pupil is identified using adaptive threshold and morphology close calculations.

e) determining a distance (d) of the reflected light spot 42 from the center 41 of the pupil and an angle (θ) of the reflected light spot 42 from a vertical axis 43 passing through the center 41 of the pupil;

In this sub-step, the distance (d) of the reflected light spot 42 from the center 41 of the pupil is determined using the equation $$d = \sqrt{[(x_1-x_2)^2 + (y_1-y_2)^2]}$$

and the angle (θ) of the reflected light spot 42 from the vertical axis 43 passing through the center 41 of the pupil is determined using the equation $$\theta = \tan^{-1}\left[\frac{y_1 - y_2}{x_1 - x_2}\right]$$

where $x_1$ and $y_1$ are the coordinates of the center 41 of the pupil, and $x_2$ and $y_2$ are the coordinates of the reflected light spot 42.

It is noted that when the angle (θ) determined in this sub-step is negative, e.g., −60 degrees, the angle (θ) is converted into an angle supplement of the angle (θ), i.e., 120 degrees.

f) obtaining a candidate point, e.g., the candidate point (c1), the coordinates of which are the distance (d) and the angle (θ) determined in sub-step e), whereby the candidate point (c1) corresponds to the predefined region (r1) indicated in sub-step b); and g) repeating sub-steps b) to f) until the candidate points (c1 to c16) corresponding to all of the predefined regions (r1 to r16) are obtained, as best shown in FIG. 4.

It is noted that, in step 21, when the predefined regions (r1 to r16) are indicated in a sequential manner starting from the predefined region (r1), as illustrated in FIGS. 6a to 6d, the distances (d) corresponding to the predefined regions (r1, r2, r3, r4) will vary slightly. Moreover, the angles (θ) corresponding to the predefined regions (r1, r2, r3, r4) will vary considerably. Further, the distance (d) corresponding to the predefined region (r1) will be longer than that corresponding to the predefined region (r5), the distance (d) corresponding to the predefined region (r5) will be longer than that corresponding to the predefined region (r9), and the distance (d) corresponding to the predefined region (r9) will be longer than that corresponding to the predefined region (r13). Still further, the angles (θ) corresponding to the predefined regions (r1, r5, r9, r13) will vary slightly.

In step 22, while the user is gazing at the screen module 14 and the light source 11 emits light toward the eye 4 of the user, the gazing point-determining unit 132 of the computing module 13 acquires an image 401 of the eye 4 of the user captured by the image-capturing module 12.

In step 23, the gazing point-determining unit 132 of the computing module 13 identifies a center 41 of a pupil of and a reflected light spot 42 on the eye 4 from the image 401 acquired in step 22.

In step 24, the gazing point-determining unit 132 of the computing module 13 determines a distance (d) of the reflected light spot 42 from the center 41 of the pupil and an angle (θ) of the reflected light spot 42 from a vertical axis 43 passing through the center 41 of the pupil.

In step 25, the gazing point-determining unit 132 of the computing module 13 determines a gazing point based on the distance (d) and the angle (θ) determined in step 24 and the candidate points (c1 to c16) in the pre-established set of data 133.

In this embodiment, step 25 includes the sub-steps of:

defining a point 5 (see FIG. 4), the coordinates of which are the distance (d) and the angle (θ) determined in step 24;

finding one of the candidate points (c1 to c16), e.g., the candidate point (c6), in the pre-established set of data 133 that has a minimum distance from the point 5; and regarding the candidate point (c6) thus found as the gazing point.

Preferably, the candidate point having the minimum distance is found using a minimum object function, which is defined as $$w_1 * |x_1' - x_2'| + w_2 * |y_1' - y_2'|$$

where $x_1'$ and $y_1'$ are the coordinates of one of the candidate points (c1 to c16) in the pre-established set of data 133, $x_2'$ and $y_2'$ are the coordinates of the point 5, $w_1$ is a weight assigned to $|x_1' - x_2'|$, and $w_2$ is a weight assigned to $|y_1' - y_2'|$.

In step 26, the processing module 15 performs an operation associated with the gazing point.

In this step, the processing module 15 moves a cursor 101 on the screen module 14 to the gazing point.

From the above description, it can be deduced that the accuracy at which the eye-tracking method of this embodiment determines the gazing point can be enhanced by simply increasing the number of candidate points in the pre-established set of data 133.

The second preferred embodiment of an eye-tracking method to be implemented by the aforementioned system 1 according to this invention will now be described with further reference to FIG. 7.

In step 71, the data-establishing unit 131 of the computing module 13 obtains a pre-established set of data.

Figures 7, 8:
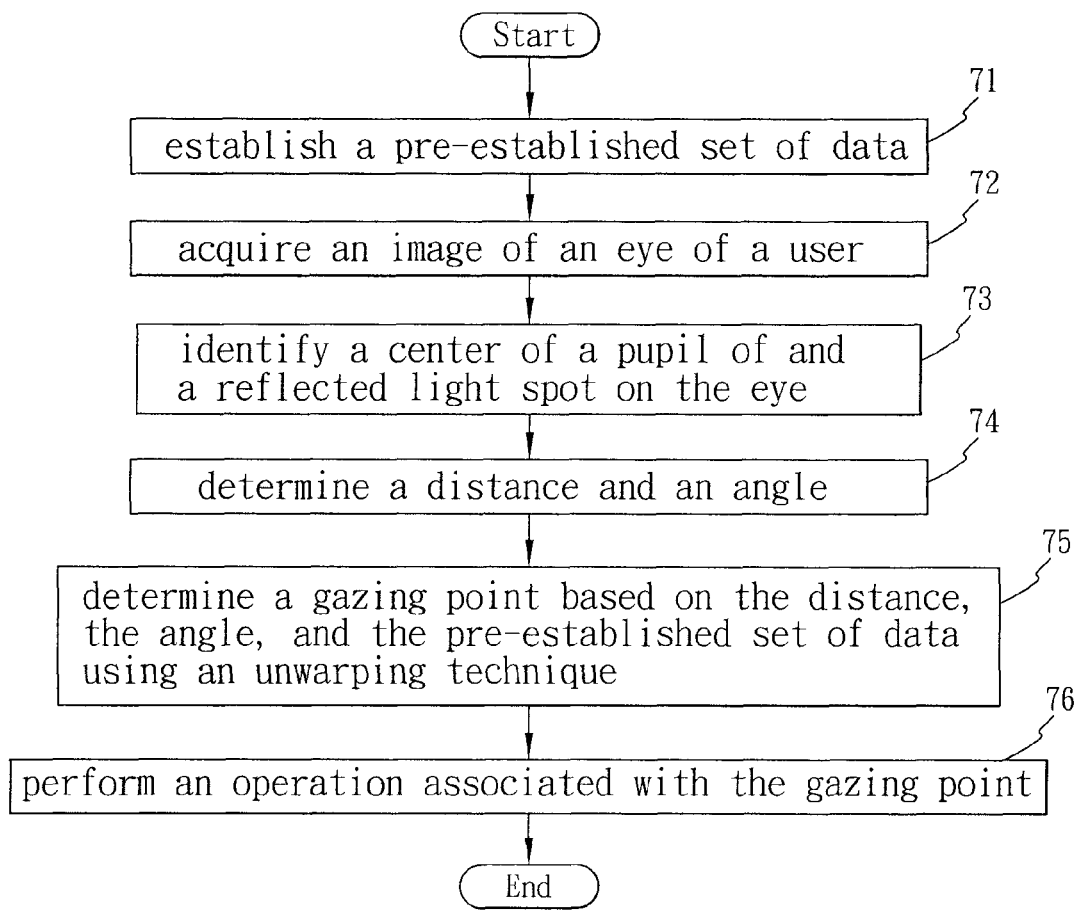
FIG. 7 is a flow chart of the second preferred embodiment of an eye-tracking method to be implemented by the system shown in FIG. 1 according to this invention.
FIG. 8 is a schematic diagram illustrating the screen module when partitioned by the system into six predefined regions.

In this embodiment, step 71 includes the following sub-steps:

i) partitioning the screen module 14 into predefined regions;

In this sub-step, as illustrated in FIG. 8, the screen module 14 is partitioned into six predefined regions (r1 to r6).

ii) defining coordinates corresponding to each of the predefined regions (r1 to r6);

iii) controlling the screen module 14 to indicate, i.e., to show, one of the predefined regions (r1 to r6) e.g., the predefined region (r1);

iv) while the user is gazing at the predefined region (r1) indicated in sub-step iii) and the light source 11 emits light toward the eye 4 of the user, acquiring an image 401 of the eye 4 of the user captured by the image-capturing module 12;

v) identifying a center 41 of a pupil of and a reflected light spot 42 on the eye 4 from the image 401 acquired in sub-step iv);

vi) determining a distance (d) of the reflected light spot 42 from the center 41 of the pupil and an angle (θ) of the reflected light spot 42 from a vertical axis 43 passing through the center 41 of the pupil;

vii) repeating sub-steps iii) to vi) until the distances (d) and the angles (θ) corresponding to all of the predefined regions (r1 to r6) are determined; and viii) obtaining coefficients based on the coordinates corresponding to the predefined regions (r1 to r6) defined in sub-step ii) and the distances (d) and the angles (θ) corresponding to the predefined regions (r1 to r6).

In this sub-step, the coefficients ($a_0$ to $a_5$, $b_0$ to $b_5$) are obtained using equations $$u = a_0 + a_1 x + a_2 y + a_3 x^2 + a_4 xy + a_5 y^2, \text{ and}$$

$$v = b_0 + b_1 x + b_2 y + b_3 x^2 + b_4 xy + b_5 y^2$$

where u and v are the coordinates of one of the predefined regions (r1 to r6) defined in sub-step ii), and x and y are the distance (d) and the angle (θ) determined in sub-step vi), respectively.

It is noted that, in step 71, since the screen module 14 is partitioned into six predefined regions (r1 to r6), six coordinates $(u_1, v_1)$, $(u_2, v_2)$, $(u_3, v_3)$, $(u_4, v_4)$, $(u_5, v_5)$, $(u_6, v_6)$ can be defined, and six distances $(d_1, d_2, d_3, d_4, d_5, d_6)$ and six angles $(\theta_1, \theta_2, \theta_3, \theta_4, \theta_5, \theta_6)$ can be determined. As such, when each of the coordinates $(u_1, v_1)$, $(u_2, v_2)$, $(u_3, v_3)$, $(u_4, v_4)$, $(u_5, v_5)$, $(u_6, v_6)$, the corresponding one of the distances $(d_1, d_2, d_3, d_4, d_5, d_6)$, and the corresponding one of the angles $(\theta_1, \theta_2, \theta_3, \theta_4, \theta_5, \theta_6)$ are introduced into the aforementioned equations, twelve equations can be derived, from which the coefficients ($a_0$ to $a_5$, $b_0$ to $b_5$) are obtained using, for example, singular value decomposition (SVD) calculations.

In step 72, while the user is gazing at the screen module 14 and the light source 11 emits light toward the eye 4 of the user, the gazing point-determining unit 132 of the computing module 13 acquires an image 401 of the eye 4 of the user captured by the image-capturing module 12.

In step 73, the gazing point-determining unit 132 of the computing module 13 identifies a center 41 of the pupil of and a reflected light spot 42 on the eye 4 from the image 401 acquired in step 72.

In step 74, the gazing point-determining unit 132 of the computing module 13 determines a distance (d) of the reflected light spot 42 from the center 41 of the pupil and an angle (θ) of the reflected light spot 42 from a vertical axis 43 passing through the center 41 of the pupil.

In step 75, the gazing point-determining unit 132 of the computing module 13 determines a gazing point based on the distance (d) and the angle (θ) determined in step 74 and the coefficients ($a_0$ to $a_5$, $b_0$ to $b_5$) in the pre-established set of data.

In this embodiment, step 75 is performed using an unwarping technique, which calculates the coordinates (u', v') of the gazing point using the equations $$u' = a_0 + a_1 x' + a_2 y' + a_3 x'^2 + a_4 x' y' + a_5 y'^2, \text{ and}$$

$$v' = b_0 + b_1 x' + b_2 y' + b_3 x'^2 + b_4 x' y' + b_5 y'^2$$

where $a_0$ to $a_5$ and $b_0$ to $b_5$ are the coefficients in the pre-established set of data, and x' and y' are the distance (d) and the angle (θ) determined in step 74, respectively.

In step 76, the processing module 15 performs an operation associated with the gazing point.

It is noted that the accuracy at which the gazing point is determined in this embodiment is substantially the same as that of the previous embodiment.

From the above description, the pre-established set of data is obtained by simply partitioning the screen module 14 into six predefined regions (r1 to r6). The pre-established set of data of the eye-tracking method of this embodiment is therefore easier and faster to obtain than that of the previous embodiment without sacrificing the accuracy at which the gazing point is determined.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. An eye-tracking method adapted to be implemented by a system, said eye-tracking method comprising:

A) while a user is gazing at a screen module and a light source emits light toward an eye of the user, configuring the system to acquire an image of the eye of the user captured by an image-capturing module;

B) configuring the system to identify a pupil of and a reflected light spot on the eye from the image acquired in step A);

C) configuring the system to determine a distance of the reflected light spot from a reference point on the pupil and an angle of the reflected light spot from an axis passing through the reference point on the pupil;

D) configuring the system to determine a gazing point based on the distance and the angle determined in step C) and a pre-established set of data obtained based on predefined regions on the screen module; and E) configuring the system to perform an operation associated with the gazing point.

2. The eye-tracking method as claimed in claim 1, wherein the pre-established set of data includes a plurality of candidate points, each of which corresponds to a respective one of the predefined regions and is defined by coordinates, and step D) includes the sub-steps of:

d1) configuring the system to define a point, the coordinates of which are the distance and the angle determined in step C);

d2) configuring the system to find one of the candidate points in the pre-established set of data that has a minimum distance from the point defined in sub-step d1); and d3) configuring the system to regard the candidate point found in sub-step d2) as the gazing point.

3. The eye-tracking method as claimed in claim 2, wherein sub-step d2) is performed using a minimum object function, which is defined as $$w_1 * |x_1' - x_2'| + w_2 * |y_1' - y_2'|$$

where $x_1'$ and $y_1'$ are the coordinates of one of the candidate points in the pre-established set of data, $x_2'$ and $y_2'$ are the coordinates of the point defined in sub-step d1), $w_1$ is a weight assigned to $|x_1' - x_2'|$, and $w_2$ is a weight assigned to $|y_1' - y_2'|$.

4. The eye-tracking method as claimed in claim 2, further comprising F) obtaining the pre-established set of data prior to step A).

5. The eye-tracking method as claimed in claim 4, wherein step F) includes the sub-steps of:
   f1) configuring the system to partition the screen module into the predefined regions;
   f2) configuring the system to control the screen module to indicate one of the predefined regions;
   f3) while the user is gazing at the predefined region indicated in sub-step f2) and the light source emits light toward the eye of the user, configuring the system to acquire an image of the eye of the user captured by the image-capturing module;
   f4) configuring the system to identify a pupil of and a reflected light spot on the eye from the image acquired in sub-step f3);
   f5) configuring the system to determine a distance of the reflected light spot from a reference point on the pupil and an angle of the reflected light spot from an axis passing through the reference point on the pupil;
   f6) configuring the system to obtain a candidate point, the coordinates of which are the distance and the angle determined in sub-step f5), whereby the candidate point corresponds to the predefined region indicated in sub-step f2); and
   f7) configuring the system to repeat sub-steps f2) to f6) until the candidate points corresponding to all of the predefined regions are obtained.

6. The eye-tracking method as claimed in claim 1, wherein step D) is performed using an unwarping technique.

7. The eye-tracking method as claimed in claim 6, further comprising F) obtaining the pre-established set of data prior to step A).

8. The eye-tracking method as claimed in claim 7, wherein step F) includes the sub-steps of:
   f1) configuring the system to partition the screen module into the predefined regions;
   f2) configuring the system to define coordinates corresponding to each of the predefined regions;
   f3) configuring the system to control the screen module to indicate one of the predefined regions;
   f4) while the user is gazing at the predefined region indicated in sub-step f3) and the light source emits light toward the eye of the user, configuring the system to acquire an image of the eye of the user captured by the image-capturing module;
   f5) configuring the system to identify a pupil of and a reflected light spot on the eye from the image acquired in sub-step f4);
   f6) configuring the system to determine a distance of the reflected light spot from a reference point on the pupil and an angle of the reflected light spot from an axis passing through the reference point on the pupil, whereby the distance and the angle correspond to the predefined region indicated in sub-step f3);
   f7) configuring the system to repeat sub-steps f3) to f6) until the distances and the angles corresponding to all of the predefined regions are determined; and
   f8) configuring the system to obtain coefficients based on the coordinates corresponding to the predefined regions defined in sub-step f2) and the distances and the angles corresponding to the predefined regions.

9. The eye-tracking method as claimed in claim 8, wherein, in sub-step f8), the coefficients $a_0$ to $a_5$ and $b_0$ to $b_5$ are obtained using equations $$u = a_0 + a_1 x + a_2 y + a_3 x^2 + a_4 xy + a_5 y^2, \text{ and}$$

$$v = b_0 + b_1 x + b_2 y + b_3 x^2 + b_4 xy + b_5 y^2$$

where u and v are the coordinates of one of the predefined regions defined in sub-step f2), and x and y are the distance and the angle determined in sub-step f6).

10. The eye-tracking method as claimed in claim 1, wherein the pre-established set of data includes a plurality of coefficients, and step D) is performed using an unwarping technique, which calculates coordinates (u', v') of the gazing point using equations $$u' = a_0 + a_1 x' + a_2 y' + a_3 x'^2 + a_4 x' y' + a_5 y'^2, \text{ and}$$

$$v' = b_0 + b_1 x' + b_2 y' + b_3 x'^2 + b_4 x' y' + b_5 y'^2$$

where $a_0$ to $a_5$ and $b_0$ to $b_5$ are the coefficients in the pre-established set of data, and x' and y' are the distance and the angle determined in step C).

11. The eye-tracking method as claimed in claim 1, wherein step E) includes the sub-step of moving a cursor on the screen module to the gazing point.

12. A system adapted to be coupled to an image-capturing module and a screen module, comprising:
   a computing module operable
      to acquire an image of an eye of a user captured by the image-capturing module while the user is gazing at the screen module and a light source emits light toward the eye of the user,
      to identify a pupil of and a reflected light spot on the eye from the image acquired from the image-capturing module,
      to determine a distance of the reflected light spot from a reference point on the pupil and an angle of the reflected light spot from an axis passing through the reference point on the pupil, and
      to determine a gazing point based on the distance and the angle determined thereby and a pre-established set of data obtained based on predefined regions on the screen module; and
   a processing module coupled to said computing module and operable to perform an operation associated with the gazing point.

13. The system as claimed in claim 12, wherein the pre-established set of data includes a plurality of candidate points, each of which corresponds to a respective one of the predefined regions and is defined by coordinates, said computing module determining the gazing point by
   defining a point, the coordinates of which are the distance and the angle determined thereby,
   finding one of the candidate points in the pre-established set of data that has a minimum distance from the point defined thereby, and
   regarding the candidate point found thereby as the gazing point.

14. The system as claimed in claim 13, wherein said computing module is further operable so as to obtain the pre-established set of data.

15. The system as claimed in claim 14, wherein said computing module obtains the pre-established set of data by obtaining the candidate points corresponding to all of the predefined regions, said computing module obtaining each of the candidate points by
- partitioning the screen module into the predefined regions,
- controlling the screen module to indicate one of the predefined regions,
- acquiring an image of the eye of the user captured by the image-capturing module while the user is gazing at the predefined region indicated by the screen module and the light source emits light toward the eye of the user,
- identifying a pupil of and a reflected light spot on the eye from the image acquired from the image-capturing module,
- determining a distance of the reflected light spot from a reference point on the pupil and an angle of the reflected light spot from an axis passing through the reference point on the pupil, and
- obtaining a candidate point, the coordinates of which are the distance and the angle thus determined, whereby the candidate point corresponds to the predefined region indicated by the screen module.

16. The system as claimed in claim 13, wherein said computing module finds said one of the candidate points in the pre-established set of data using a minimum object function, which is defined as $$w_1 * |x_1' - x_2'| + w_2 * |y_1' - y_2'|$$

where $x_1'$ and $y_1'$ are the coordinates of one of the candidate points in the pre-established set of data, $x_2'$ and $y_2'$ are the coordinates of the point defined by said computing module, $w_1$ is a weight assigned to $|x_1' - x_2'|$, and $w_2$ is a weight assigned to $|y_1' - y_2'|$.

17. The system as claimed in claim 12, wherein said computing module determines the gazing point using an unwarping technique.

18. The system as claimed in claim 17, wherein said computing module is further operable so as to obtain the pre-established set of data.

19. The system as claimed in claim 18, wherein:
said computing module obtains the pre-established set of data by
- defining coordinates corresponding to each of the predefined regions,
- determining a distance and an angle corresponding to each of the predefined regions, and
- obtaining the coefficients based on the coordinates defined thereby and the distances and the angles determined thereby; and said computing module determines the distance and the angle corresponding to each of the predefined regions by
- partitioning the screen module into the predefined regions,
- controlling the screen module to indicate one of the predefined regions,
- acquiring an image of the eye of the user captured by the image-capturing module while the user is gazing at the predefined region indicated by the screen module and the light source emits light toward the eye of the user,
- identifying a pupil of and a reflected light spot on the eye from the image acquired from the image-capturing module, and
- determining a distance of the reflected light spot from a reference point on the pupil and an angle of the reflected light spot from an axis passing through the reference point on the pupil, whereby the distance and the angle correspond to the predefined region indicated by the screen module.

20. The system as claimed in claim 19, wherein said computing module obtains the coefficients $a_0$ to $a_5$ and $b_0$ to $b_5$ using equations $$u = a_0 + a_1 x + a_2 y + a_3 x^2 + a_4 xy + a_5 y^2, \text{ and}$$

$$v = b_0 + b_1 x + b_2 y + b_3 x^2 + b_4 xy + b_5 y^2,$$

where u and v are the coordinates corresponding to one of the predefined regions defined by said computing module, and x and y are the distance and the angle determined by said computing module.

21. The system as claimed in claim 12, wherein the pre-established set of data includes a plurality of coefficients, and said computing module determines the gazing point using an unwarping technique, which calculates coordinates (u', v') of the gazing point using equations $$u' = a_0 + a_1 x' + a_2 y' + a_3 x'^2 + a_4 x'y' + a_5 y'^2, \text{ and}$$

$$v' = b_0 + b_1 x' + b_2 y' + b_3 x'^2 + b_4 x'y' + b_5 y'^2,$$

where $a_0$ to $a_5$ and $b_0$ to $b_5$ are the coefficients in the pre-established set of data, and x' and y' are the distance and the angle determined by said computing module.

22. The system as claimed in claim 12, wherein the operation associated with the gazing point includes moving a cursor on the screen module to the gazing point.

23. A computer program product, comprising:
a machine readable storage medium having program instructions stored therein which when executed cause a system to perform a set of operations including:
A) while a user is gazing at a screen module and a light source emits light toward an eye of the user, acquiring an image of the eye of the user captured by an image-capturing module;
B) identifying a pupil of and a reflected light spot on the eye from the image acquired in step A);
C) determining a distance of the reflected light spot from a reference point on the pupil and an angle of the reflected light spot from an axis passing through the reference point on the pupil;
D) determining a gazing point based on the distance and the angle determined in step C) and a pre-established set of data obtained based on predefined regions on the screen module; and
E) performing an operation associated with the gazing point.

* * * * *